United States Patent [19]

Inamoto et al.

[11] 3,932,492

[45] Jan. 13, 1976

[54] PROCESS FOR PREPARING NEW AMIDINE COMPOUNDS

[75] Inventors: Yoshiaki Inamoto; Koji Aigami, both of Wakayama, Japan

[73] Assignee: Kao Soap Co., Ltd., Tokyo, Japan

[22] Filed: Nov. 7, 1974

[21] Appl. No.: 521,855

[30] Foreign Application Priority Data

Nov. 14, 1973 Japan............................ 48-127930

[52] U.S. Cl.......... 260/501.14; 260/564 R; 424/326
[51] Int. Cl.²...................................... C07C 123/00
[58] Field of Search.................... 260/564 R, 501.14

[56] References Cited
UNITED STATES PATENTS 3,732,305   5/1973   Bauer.............. 260/564 R

FOREIGN PATENTS OR APPLICATIONS 448,469   1936   United Kingdom............. 260/564 R

OTHER PUBLICATIONS

Shriner, Chem. Reviews, Vol. 35, pp. 354–359, (1944).

*Primary Examiner*—Gerald A. Schwartz
*Attorney, Agent, or Firm*—Woodhams, Blanchard and Flynn

[57] ABSTRACT

New amidine compounds of formula (I):

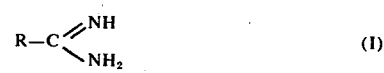

(I)

wherein R represents

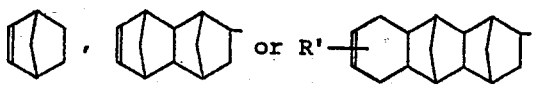

($R'$ being H or $CH_3$) and acid addition salts thereof, are prepared by reacting a nitrile of formula (II):

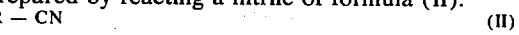

(II)

wherein R represents

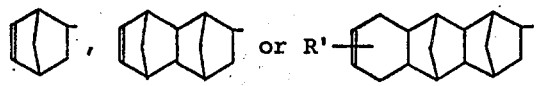

($R'$ being H or $CH_3$) with a metal amide or with an alcohol and an acid under anhydrous conditions and the product thus obtained is reacted with ammonia.

2 Claims, No Drawings

PROCESS FOR PREPARING NEW AMIDINE COMPOUNDS

BACKGROUND OF THE INVENTION

Field of the Invention

The present invention relates to a process for preparing new amidine compounds of the formula:

(I)

wherein R represents

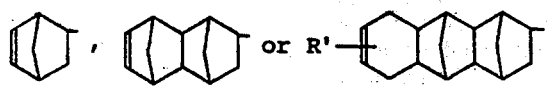

(R' being H or CH$_3$) and acid addition salts thereof.

Compounds (I) prepared by the process of the present invention are new compounds which have never been disclosed in literatures. Those amidine compounds have a special broad antimicrobial spectrum. Surprisingly, they have only a low toxicity to fish and, therefore, the use of them for various purposes can be expected. The amidine compounds are also useful as intermediates in the preparation of many heterocyclic compounds. In addition, the nitriles of formula (II):

R — CN (II)

wherein R represents

(R' being H or CH$_3$), used as starting compound can be obtained very easily from inexpensive cyclopentadiene, butadiene, isoprene, acrylonitrile, etc. by Diels-Alder reaction on a commercial scale. Thus, the amidine compounds (I) are very advantageous.

A process for synthesizing nitriles (II) has been disclosed in the specification of Japanese Pat. No. 49753/1973.

SUMMARY OF THE INVENTION

After intensive investigations on the reactions of nitriles and processes for synthesizing derivatives thereof, the inventors have found that amidines can be obtained by reacting a nitrile (II) which will be shown below with a lower alcohol and an acid in the same manner as in case of long chain aliphatic nitriles and then reacting the product with ammonia or by reacting said nitrile (II) with an alkali metal amide and hydrolyzing the resulting product. The inventors have attained the present invention on the basis of the finding.

The present invention provides a process for preparing amidines of above formula (I) and acid addition salts thereof in a simple, advantageous manner by reacting a nitrile of the formula:

R — CN (II)

wherein R has the same meaning as in formula (I) with a lower alcohol and an acid and then reacting the product with ammonia or by reacting said nitrile (II) with an alkali metal amide and hydrolyzing the resulting product.

Embodiments of the present invention will be shown below. This reaction operation is very simple. An acid is added to a mixture of a nitrile of formula (II) and a lower alcohol while the mixture is cooled externally to form an imino ether. As the acid, hydrogen halides, particularly hydrogen chloride, are most generally used. In addition, sulfuric acid, sulfonic acid, etc. are also effective. Suitable lower alcohols are methanol, ethanol, n-propanol, i-propanol, n-butanol, i-butanol and sec.-butanol. Those lower alcohols are used in a stoichiometric quantity on the basis of the nitrile to yield sufficient effect. However, no bad effects occur even if an excess of the lower alcohol is used. The reaction temperature is within the range of 0°–100°C, preferably 0°–50°C. Then, the imino ether thus obtained is dissolved in a lower alcohol of the above kind and is reacted with ammonia. Temperature for this reaction is within the range of 20°–100°C, preferably 30°–60°C.

Amidines of formula (I) can also be prepared in one step, not through the intermediate imino ether, in the following manner. The nitrile of the formula (II) is reacted with an alkali metal amide such as sodium amide or potassium amide in an anhydrous solvent such as benzene, toluene, xylene, anisole, biphenyl or liquid ammonia and then the product thus obtained is hydrolyzed. The reaction temperature is within the range of from −30°C to 150°C, preferably 10°–80°C.

The amidine thus obtained can be converted easily to the desired salts by anion exchange or by mere neutralization in the usual manner. The acid addition salts of amidine compounds obtained by the process of the present invention include those formed from organic acids and inorganic acids such as salts of hydrochloric acid, sulfuric acid, thiosulfuric acid, p-toluenesulfonic acid, oxalic acid, citric acid and phosphoric acid.

The present invention will be illustrated by way of examples to show embodiments of the invention and to show that the compounds obtained by the process of the present invention have only a low toxicity to fish and a broad antimicrobial spectrum.

EXAMPLE 1

Ten grams of nitrile (II) wherein R represents

were dissolved in 25 g of anhydrous ethanol. Hydrogen chloride was bubbled into the solution at a rate of 50 ml./min. for 90 minutes while the temperature was kept at 5°C by external ice-cooling. Thereafter, excess hydrogen chloride and ethanol were removed to obtain a colorless powder. The powder was then dissolved in 30 ml. of ethanol. The solution was heated to 40°C. Gaseous ammonia was introduced therein at a rate of 50 ml./min. for 2 hours. Thereafter, ethanol was removed under reduced pressure to obtain 10.2 g of the desired amidine hydrochloride.

Elementary analysis: Found: C;55.8 H;7.3 N;15.2 Cl;21.0. Theoretical: C;55.65 H;7.59 N;16.22 Cl;20.53. Melting point: 200°–203°C (decomposition). IR Spectrum (Nujol cm$^{-1}$): 3220 (S), 3050 (S), $\nu$N—H; 1670 (S), $\nu$N=C; 1570 (W), $\nu$C=O.

EXAMPLE 2

Four hundred grams of nitrile (II) wherein R represents

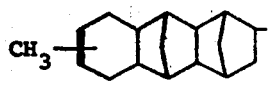

were dissolved in 96 g of anhydrous ethanol. Hydrogen chloride was bubbled into the solution at a rate of 300 ml./min. for four hours while the temperature was kept at 10°C by external ice-cooling. Then dry nitrogen gas was introduced therein to remove excess hydrogen chloride from the reaction system. Four hundred grams of anhydrous ethanol were added to the reaction mixture and the whole was heated to 50°C. Gaseous ammonia was bubbled therein at a rate of 500 ml./min. for three hours. Upon cooling, the resulting precipitate was collected by filtration and the filtrate was concentrated under reduced pressure. Ether was added to the crude product to obtain 260 g of the desired amidine hydrochloride as colorless crystals.

Elementary analysis: Found: C;70.5 H;8.4 N;9.5 Cl;11.4. Theoretical: C;70.45 H;8.87 N;9.13 Cl;11.55. Melting point: 140°–145°C. IR Spectrum (Nujol, cm$^{-1}$); 3230 (S), 3030 (S), $\nu$N—H; 1680 (S), $\nu$N=C.

EXAMPLE 3

Six grams of nitrile (II) wherein R represents

were dissolved in 80 ml. of anhydrous benzene. Two grams of finely powdered sodium amide were added slowly to the solution and the whole was subjected to the reaction under reflux for 10 hours. After completion of the reaction, the reaction mixture was added dropwise to a 5% solution of sulfuric acid in ice-water under stirring to precipitate colorless crystals. The crystals was collected by filtration, washed with water and dried under reduced pressure to obtain 3.1 g of the desired amidine sulfate.

Elementary analysis: Found: C;61.5 H;7.4 N;10.8 S;6.9. Theoretical: C; 62.12 H;7.62 N;11.15 S;6.38. Melting point: 240°–244°C. IR Spectrum (Nujol, cm$^{-1}$); 3270 (S), 3030 (S), $\nu$N—H 1680 (S), $\nu$N=O 1090 (VS), 1080 (VS), 1060 (VS), $\nu$S=O.

EXAMPLE 4

Ten grams of the amidine hydrochloride obtained in Example 2 were dissolved in 100 ml. of water. Twenty-five milliliters of 10% aqueous sodium sulfate solution were added dropwise to the above solution under stirring at room temperature to obtain colorless crystals. The crystals were collected by filtration, washed with water and dried under reduced pressure to obtain 9.8 g of the desired amidine sulfate.

Elementary analysis: Found: C;67.3 H;8.3 N;8.4 S;4.8. Theoretical: C;67.68 H;8.52 N;8.77 S;5.02. Melting point: 235°–237°C (decomposition). IR Spectrum (Nujol, cm$^{-1}$): 3280 (m), 3040 (m), $\nu$N—H; 1680 (m), $\nu$C=N; 1140 (vs, br), $\nu$S=O.

EXAMPLE 5

Minimum inhibiting concentrations (MIC) of the compounds prepared according to the present invention for bacteria and moulds are summarized in Table 1. MIC was determined according to a series of dilution tests.

As culture medium, broth medium was used for bacteria and Sabouraud-Agar medium was used for moulds.

Table 1

Antimicrobial activity

| Compound | E.coli | St.aureus | B.subtilis | Pseu. aeruginosa | Asp.niger | Pen. citrinum |
|---|---|---|---|---|---|---|
| | ppm | ppm | ppm | ppm | ppm | ppm |
| (structure 1) | 20–40 | 5–10 | 5–10 | 40–60 | 80–100 | 120–140 |
| (structure 2) | 25–50 | 25–50 | — | — | 120–140 | 120–140 |

EXAMPLE 6

Table 2 shows the results of tests of a toxicity of compound prepared according to the present invention and benzalkonium chloride (control) to fish. The test was carried out according to plant waste water test method (JIS–K–0102–1964). Wakin goldfish was used as the subject.

Table 2
Toxicity to fish

| Compound | TLM* |
|---|---|
| 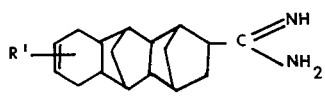 | 11.5 ppm |
| Benzalkonium chloride | 0.87 |

*A concentration at which half the number of the subjects died within 48 hours. The higher the number of ppm., the lower the toxicity to fish.

The embodiments of the invention in which an exclusive property or privilege is claimed are defined as follows:

1. An amidine compound having the formula wherein R' is H or $CH_3$, or an antimicrobially effective acid addition salt thereof.

2. An amidine compound as claimed in claim 1 in which the acid moiety consists of an acid selected from the group consisting of hydrochloric acid, sulfuric acid, thiosulfuric acid, p-toluenesulfonic acid, oxalic acid, citric acid and phosphoric acid.

* * * * *